United States Patent [19]

Schermanz et al.

[11] Patent Number: 5,202,478

[45] Date of Patent: Apr. 13, 1993

[54] PROCESS FOR THE PREPARATION OF ALPHA, OMEGA-ALKANEDIOIC ACIDS

[75] Inventors: Karl Schermanz, Graz; Manfred Schöftner, Linz; Engelbert Kloimstein, Eferding; Josef Schaller, Linz; Eduard Perndorfer, Traun; Klaus Reiter; Rudolf Neuhofer, both of Linz, all of Austria

[73] Assignee: Chemie Linz Gesellschaft M.B.H., Linz, Austria

[21] Appl. No.: 626,292

[22] Filed: Dec. 12, 1990

[30] Foreign Application Priority Data

Dec. 14, 1989 [AT] Austria .................. 2839/89

[51] Int. Cl.$^5$ ................. C07C 51/16; C07C 51/235
[52] U.S. Cl. ................................ 562/531
[58] Field of Search ............................ 562/531

[56] References Cited

U.S. PATENT DOCUMENTS 4,769,464  9/1988  Sajtos ...................... 546/314

FOREIGN PATENT DOCUMENTS 250466   3/1964  Australia ................... 562/531
1518945  8/1969  Fed. Rep. of Germany .
2945004  5/1980  Fed. Rep. of Germany .
2942279  4/1981  Fed. Rep. of Germany .

OTHER PUBLICATIONS

Chem. Abstr. 96 col. 199107a (1982)=JA 32245/1982.
Chem. Abstr. 97 col. 216903x (1982)=JA 142940/1982.

*Primary Examiner*—José G. Dees
*Assistant Examiner*—Joseph M. Conrad, III
*Attorney, Agent, or Firm*—Wenderoth, Lind & Ponack

[57] ABSTRACT

Process for the preparation of alpha, omega-alkanedicarboxylic acids of the general formula I

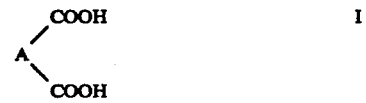

in which A is an alkylene radical having 4–14 C atoms by reacting a cycloalkene of the general formula II

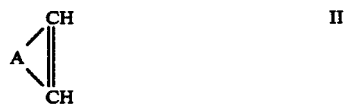

in which A has the abovementioned meaning with ozone in the presence of an inert solvent, catalytically hydrogenating the peroxide solution formed, followed by oxidation of the dialdehyde formed to the diacid of the formula I in the presence of an inert aprotic solvent.

9 Claims, No Drawings

PROCESS FOR THE PREPARATION OF ALPHA, OMEGA-ALKANEDIOIC ACIDS

The invention relates to a process for the preparation of alpha, omega-alkanedicarboxylic acids, starting from cycloalkenes and alpha, omega-alkanedialdehydes.

Alpha, omega-alkanedicarboxylic acids are valuable starting materials in the chemical industry and are used, for example, in the preparation of pharmaceuticals, cosmetics, lubricants and the like.

Processes for the preparation of alpha, omega-alkanedicarboxylic acids are already known.

Thus, for example, in Chemical Abstracts Vol 96, (1982) 199107 a, the preparation of alpha, omega-alkanedicarboxylic acids by oxidative ring cleavage of the corresponding cycloalkenes by means of ozone in the presence of methanol and sulphuric acid, oxidation of the peroxide solution with $H_2O_2$, followed by hydrolysis of the dimethyl esters formed is described, after which the dicarboxylic acid formed has to be purified by recrystallization.

Furthermore, the ozonization of cyclooctene in propionic acid to give acyloxy hydroperoxide, which rearranges to omega-formylcarboxylic acid, followed by oxidation of this solution with $H_2O_2$ in the presence of an organic acid to give the dicarboxylic acid, which also has to recrystallized, is known from Chemical Abstracts Vol 97 (1982) 216903x.

A serious disadvantage of these two processes is that an oxidizing agent has to be added to a peroxide-containing solution. A reaction mixture consisting of a peroxide and a further oxidizing agent represents a combination which is very prone to explosive decomposition. The application of such a process on a large scale is therefore questionable for safety reasons.

A risk-free process for the preparation of alpha, omega-alkanedicarboxylic acids has now been found in which, starting from cycloalkenes, alkanedicarboxylic acids are obtained. In this process, the cycloalkenes which serve as starting compounds are treated with ozone, the peroxide-containing ozonide solution formed in the ozonization is hydrogenated catalytically, and the dialdehyde formed is then oxidized to the diacid. The dangerous peroxides are destroyed with the reduction of the peroxide-containing solution, and the oxidation takes place in peroxide-free solution, thus no longer giving rise to the risk of explosion. The alkanedicarboxylic acids are formed in high purity in this process.

Accordingly, the invention relates to a process for the preparation of alpha, omega-alkanedicarboxylic acids of the general formula I

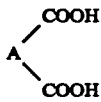

I in which A is an alkylene radical having 4–14 C atoms, which process is characterized in that a cycloalkene of the general formula II

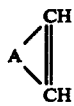

II in which A has the abovementioned meaning is reacted with ozone in the presence of a solvent, the peroxide solution formed is hydrogenated catalytically, followed by oxidation of the dialdehyde formed to the diacid of the formula I in the presence of an inert aprotic solvent.

In formulae I and II, A is an alkylene radical having 4 to 14 C atoms, for example a butylene, pentylene, hexylene, heptylene, octylene, nonylene, decylene, undecylene, dodecylene, tridecylene or tetradecylene radical. A is preferably a pentylene, a hexylene or decylene radical.

The ozonization and the subsequent hydrogenation can be carried out in the usual manner. For this purpose the starting compounds are dissolved in a suitable organic solvent and treated with ozone. The solution of the ozonolysis product is then hydrogenated catalytically, using hydrogen. Suitable catalysts are novel metal catalysts usually used for hydrogenation, which can be used in the form of powdered catalyst with support materials or without support material, for example Pd, Pt, Ru, Rh, Ni catalysts. Examples of suitable support materials are activated carbon, if desired in combination with an alkaline earth metal carbonate, aluminas, silica gel and kieselguhr. Pt or Pd/C on $CaCO_3$ is preferably used as the catalyst.

Ozonization and subsequent hydrogenation are preferably carried out by the process described in U.S. Pat. No. 4,769,464. In this process the reaction is carried out by dissolving, the cycloalkene in an organic solvent in which it is readily soluble, for example in a lower aliphatic alcohol, preferably in methanol, and treated with the equivalent amount of ozone. The ozonization is carried out at temperatures of about $-30$ to $0°$ C., preferably about $-20°$ to $0°$ C.

The catalytical hydrogenation of the ozonolysis product which follows the ozonization is carried out in dilute solution, it being preferred to maintain a controlled peroxide content of at most 0.1 mol/l during the hydrogenation. For this purpose, a suspension of the catalyst in the solvent and hydrogen is initially- introduced, and the ozonolysis solution is fed in continuously. This measure keeps the peroxide content of the reaction medium at a low level and thus prevents poisoning and loss in activity of the catalyst.

The hydrogenation is carried out virtually in the absence of pressure, i.e. pressures of 1 to 3 bar, which are usually used to prevent air from entering the hydrogenation reactor.

The reaction temperature during the hydrogenation is about $20°$ to $40°$ C. The pH is maintained during the hydrogenation in a range from 2–7. Since small amounts of acid byproducts can be formed during the hydrogenation, the pH can be maintained in the desired range, if necessary, by adding a base, preferably dilute sodium hydroxide or potassium hydroxide solution. The catalyst is then filtered off, and the solvent is removed. The residue is dissolved in an inert solvent suitable for the oxidation step which follows and oxidised, using an oxidizing agent. Examples of suitable solvents are aprotic organic solvents which are inert under the reaction conditions, for example aromatic hydrocarbons, such as benzene, toluene, chlorobenzene, dichlorobenzene and the like. The oxidizing agents which can be used are conventional oxidizing agents, such as peroxides, for example $H_2O_2$, oxygen in conjunction with metal salts as the catalyst, and the like. However, it was found that the oxidation, using air or oxygen, preferably oxygen, as the oxidizing agent proceeds without having to use catalysts, such as metal salts, and yet in doing so the dicarboxylic acids are formed uniformly in high purity and excellent yields. Accordingly, oxygen or air, most preferably oxygen, is used as the oxidizing agent. The oxidation is preferably carried out under pressure, pressures of 3-10 bar being preferred. The reaction is carried out at temperatures of 50°-100° C., preferably at 70°-90° C. A process for the oxidation of an alpha, omega-dicarboxylic acid, starting from alpha, omega-dialdehydes in an inert, aprotic, organic solvent using air or oxygen as the oxidizing agent under pressure at temperatures of 50° to 100° C. is novel and also provided by the invention.

After the oxidation is complete, the reaction solution is cooled, concentrated to a certain volume, or the solvent is removed, as a result of which the dicarboxylic acid is obtained in crystalline form.

The process according to the invention gives alpha, omega-dicarboxylic acids in high purity and excellent yields. As a rule, yields of 65-85%, after workup of the mother liquor, 75-95% are obtained. The dicarboxylic acids are obtained in at least 95% purity, which usually makes further purification of the final product unnecessary.

EXAMPLE 1: DODECANEDIOIC ACID

Dodecanedial 130.1 g (1 mol) of cyclododecene (95% pure) were dissolved in 1500 ml of methanol, cooled to −20° C., and an $O_2/O_3$ mixture containing 4% by weight of ozone was introduced until 1 mol of ozone had been added to the solution. The ozonization solution obtained was then fed in continuously via a metering tank into a hydrogenation reactor into which 5 g of Pd/C on $CaCO_3$ (Lindlar catalyst) had been initially introduced and which was filled with hydrogen in such a manner that the peroxide content does not exceed 0.02 mol/l. The hydrogenation was carried out with vigorous stirring and addition of hydrogen until the test for peroxide was negative. The hydrogenation solution obtained contained 72.96% of the theory of dodecanedial (GC).

Dodecanedioic acid

The solvent was evaporated from the hydrogenation solution, and the residue dissolved in 1000 ml of chlorobenzene. Oxygen was added to the solution in an autoclave under pressure of 5 bar with stirring, and the mixture was heated to 80° C. After the reaction was complete, the autoclave was let down, the solution was cooled to room temperature, and the solutions were concentrated to about 300 ml. The resulting crystalline precipitate was filtered off and washed with water to give 151 g (0.655 mol) of dodecanedioic acid (65%, relative to cyclododecene) in 96% purity.

EXAMPLE 2

Octanedial 110.2 g (1 mol) of cyclooctene (95% pure) were dissolved in 1500 ml of methanol, cooled to −20° C., and an $O_2/O_3$ mixture containing 4% by weight of ozone was introduced until 1, mol of ozone had been added to the solution. The ozonization solution obtained was then fed in continuously via a metering tank into a hydrogenation reactor into which 5.0 g of Lindlar catalyst (Pd/C on $CaCO_3$) had been initially introduced and which was filled with hydrogen in such a manner that the peroxide content does not exceed 0.02 mol/l. The hydrogenation was carried out with vigorous stirring and addition of hydrogen until the test for peroxide was negative. The pH dropped from 7 to 5.4. The hydrogenation solution obtained contained 78.75% of the theory of octanedial.

Octanedioic acid

The solvent was removed from the hydrogenation solution, and the residue dissolved in 1000 ml of chlorobenzene. Oxygen was added to this solution in an autoclave under a pressure of 5 bar with stirring, and the temperature was kept at about 80° C. After the reaction was complete, the autoclave was let down, the solution was cooled to room temperature, and the solvent was removed down to a volume of concentrated to about 300 ml. The precipitate formed upon cooling to about 7° C. was filtered off and washed with water to give 116.2 g (0.702 mol) of octanedioic acid (70.2%) relative to cyclooctene (95% pure) used) in 98.5% purity.

What we claim is:

1. Process for the preparation of alpha, omega-alkane-dicarboxylic acids of the formula I

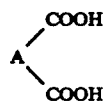

in which A is an alkylene radical having 4-14 C atoms, comprising reacting a cycloalkene of the formula II

in which A has the abovementioned meaning with ozone in the presence of an inert solvent, hydrogenating the peroxide solution formed catalytically, followed by oxidation of the dialdehyde formed to the diacid of the formula I in the presence of an inert aprotic solvent.

2. Process according to claim 1, comprising using cycloheptene, cyclooctene or cyclododecene as starting material.

3. Process according to claim 1, comprising carrying out the reaction with ozone in the presence of a lower aliphatic alcohol.

4. Process according to claim 1, comprising carrying out the reaction with the equivalent amount of ozone.

5. Process according to claim 1, comprising maintaining during the hydrogenation of the ozonolysis products a peroxide content of at most 0.1 mol/l.

6. Process according to claim 1, comprising maintaining the pH during the catalytic hydrogenation in the range of 2-7.

7. Process according to claim 1, comprising using Pd on activated carbon in combination with $CaCO_3$ or Pt as the catalyst.

8. Process according to claim 1, comprising using oxygen or air as the oxidizing agent in the oxidation step which follows the hydrogenation.

9. Process according to claim 1, comprising carrying out the oxidation at a pressure of 3-10 bar and at a temperature of 70° to 90° C.

* * * * *